(12) United States Patent
Lasarov et al.

(10) Patent No.: US 11,504,017 B2
(45) Date of Patent: Nov. 22, 2022

(54) ADAPTIVE WEARABLE DEVICE FOR PHYSIOLOGICAL MEASUREMENTS AND METHODS USING THE SAME

(71) Applicant: Nokia Technologies Oy, Espoo (FI)

(72) Inventors: Harri Lasarov, Espoo (FI); Matti Kosonen, Jarvenpaa (FI); Antti Salo, Lohja as (FI)

(73) Assignee: Nokia Technologies Oy, Espoo (FI)

( * ) Notice: Subject to any disclaimer, the term of this patent is extended or adjusted under 35 U.S.C. 154(b) by 448 days.

(21) Appl. No.: 16/086,049

(22) PCT Filed: Mar. 14, 2017

(86) PCT No.: PCT/FI2017/050163
§ 371 (c)(1),
(2) Date: Sep. 18, 2018

(87) PCT Pub. No.: WO2017/168041
PCT Pub. Date: Oct. 5, 2017

(65) Prior Publication Data
US 2020/0288999 A1   Sep. 17, 2020

(30) Foreign Application Priority Data
Mar. 31, 2016   (EP) .................................... 16163070

(51) Int. Cl.
*A61B 5/024*   (2006.01)
*A61B 5/00*   (2006.01)

(52) U.S. Cl.
CPC ........ *A61B 5/02427* (2013.01); *A61B 5/0006* (2013.01); *A61B 5/0022* (2013.01);
(Continued)

(58) Field of Classification Search
CPC . A61B 5/02427; A61B 5/0006; A61B 5/6823; A61B 5/7475; A61B 5/6824;
(Continued)

(56) References Cited

U.S. PATENT DOCUMENTS 5,243,992 A * 9/1993 Eckerle .............. A61B 5/02438
600/503
2006/0133213 A1* 6/2006 Robert ................... G04G 21/02
368/88
(Continued)

FOREIGN PATENT DOCUMENTS

| JP | S-63229303 A | 9/1988 |
|---|---|---|
| JP | 2004305268 A | 11/2004 |

(Continued)

*Primary Examiner* — Patrick Fernandes
(74) *Attorney, Agent, or Firm* — Harrington & Smith

(57) ABSTRACT

Provided are adaptive wearable devices that measure physiological conditions, methods of operating the device, and computer programs for use with the device. The adaptive wearable device provides improved reliability in data due to the adaptive structure and can be made waterproof with the incorporation of a polymer material. In the context of a wearable device, an apparatus is provided that includes a support structure configured to at least partially enclose the torso or an appendage of a user, a spring module disposed on the support structure, a first section of flexible circuitry disposed on the spring module and a first sensor disposed on the spring module and configured to monitor the user.

14 Claims, 9 Drawing Sheets

(52) U.S. Cl.
CPC .......... *A61B 5/6823* (2013.01); *A61B 5/6824* (2013.01); *A61B 5/7475* (2013.01)

(58) Field of Classification Search
CPC ... A61B 5/0022; A61B 5/024; A61B 5/02405; A61B 5/04004; A61B 5/6825; A61B 5/6826; A61B 5/6828; A61B 5/6829; A61B 5/6802; A61B 5/681; A61B 5/683; A61B 5/6843; A61B 5/6844; A61B 6/447; A61B 6/4476; A61B 5/6833; A61B 5/68335; A61B 2560/0412

See application file for complete search history.

(56) References Cited

U.S. PATENT DOCUMENTS

| | | | |
|---|---|---|---|
| 2011/0066049 A1* | 3/2011 | Matsumoto | A61B 5/02438 600/500 |
| 2015/0265214 A1* | 9/2015 | De Kok | A61B 5/681 600/301 |
| 2015/0282712 A1* | 10/2015 | Presura | A61B 5/6831 600/301 |
| 2015/0282713 A1 | 10/2015 | Fei et al. | |
| 2015/0313542 A1 | 11/2015 | Goldberg et al. | |
| 2015/0351689 A1* | 12/2015 | Adams | A61B 5/6833 600/300 |

FOREIGN PATENT DOCUMENTS

| | | | | |
|---|---|---|---|---|
| JP | 2009226024 A | 10/2009 | | |
| WO | WO-2015100499 A1 * | 7/2015 | ........... | A61B 5/7203 |
| WO | WO 2015/173464 A1 | 11/2015 | | |

* cited by examiner

ADAPTIVE WEARABLE DEVICE FOR PHYSIOLOGICAL MEASUREMENTS AND METHODS USING THE SAME

This patent application is a U.S. National Stage application of International Patent Application Number PCT/FI2017/050163 filed Mar. 14, 2017, which is hereby incorporated by reference in its entirety, which claims priority to EP 16163070.2 filed Mar. 31, 2016.

FIELD

An example embodiment of the present invention relates to a wearable device, method of using the same, and computer program for the same. The wearable device, such as an arm band, a chest belt or a wrist device, measures physiological conditions of a user.

BACKGROUND

Conventional wearable devices comprising electronic hardware including sensors are not always optimal. Difficulties can arise in providing electrical hardware and electronic components in a suitable structure, such as a curved wrist device, chest belt or arm band, which maintains stable and consistent contact with the skin of a user. Typically, electrical hardware and electronic components such as sensors are mounted on rigid circuit boards and are thus limited in their position within the device to rigid planar portions of the device. The devices may suffer from inadequate or compromised sensor measurement readings and data due to relative 3 axis movement between the sensor and skin, which varies the applied pressure and changes in the measurement location. In addition, a photodetector could be exposed to unwanted ambient light or light leakage. Moreover, previous devices may suffer from poor user comfort levels thereby preventing prolonged use or wearing of such devices.

SUMMARY

Example embodiments of the present invention provide adaptive wearable devices, methods of using such devices, and computer programs for use in such devices. Adaptive wearable devices in accordance with example embodiments of the present invention may help provide improved stability enabling more accurate and reliable measurements.

Reliable measuring (e.g., photoplethysmography (PPG), skin temperature, electro dermal activity (EDA), bio impedance, electromyography (EMG), electrocardiography (ECG) and electroencephalography (EEG)) of bio signals and vital signs needs a stable contact to the skin of a user. Stability is made difficult due to movement by the user (e.g., running, posture changes, limb movement or even breathing) and external interferences. An example embodiment of the present invention provides adaptive wearable devices that are stable on the skin of a user. The adaptive wearable device includes an improved structure that adjusts the position of an enclosed sensor in response to movement to maintain the relative position of the sensor against the skin of the user. The improved structure includes a spring module that responds to movements of the device and/or user and adjusts the position of the sensor accordingly to provide and maintain optimal location and pressure against the skin of the user. The adaptive device reduces excessively high pressure against the skin, which could interfere with the readings of the sensor. For instance, excessively high pressure against the skin could interfere with normal blood circulation in vessels. The adaptive wearable device allows for stable and consistent readings of the relevant physiological measurements by the sensor, providing more accurate and reliable data. In addition, due to the incorporation of the spring module, the sensor may be able to maintain its position against the skin of a user without the use of an adhesive.

In addition, in some embodiments, the adaptive wearable device includes a polymer material covering the sensor. The polymer material may direct light rays to the sensor and may have a slightly sticky exterior, which provides friction against the skin and thereby helps maintain the relative position of the sensor against the skin. The polymer material also helps protect the sensor and may allow the device to be waterproof.

The adaptive wearable device is easy to manufacture and can be made to have a seamless exterior. Further, the adaptive wearable device can include various sensors or electrodes for measuring physiological conditions of the user as well as external conditions of the environment. The device can be made with flexible and/or stretchable material without hindering the reliability and accuracy of the sensor(s).

According to at least some but not necessarily all examples of the disclosure there is provided an apparatus comprising: a support structure configured to at least partially enclose the torso or an appendage of a user, a spring module disposed on the support structure; a first section of flexible circuitry disposed on the support structure (e.g., on the spring module), and a first sensor disposed on the spring module and configured to monitor the user. The support structure may comprise an inner support layer and an outer support layer. In some embodiments, the inner and outer support layers are laminated or otherwise coupled together to form a seamless exterior and may enclose components of the support structure, such as circuitry, when coupled together. In some embodiments, the spring module comprises one or more ledge, dome, spiral, or foam springs.

In certain embodiments of the present disclosure, the apparatus further comprises a polymer material as a protective layer disposed over the first sensor. The polymer material may be transparent and direct light rays to the sensor. The polymer material may have a slightly sticky exterior, which provides friction against the skin and thereby helps maintain the relative position of the sensor against the skin. The polymer material may be any suitable material and may be a thermoset, thermoplastic, or even two component materials. For instance, the polymer material may comprise one or more of poly(methyl metacrylate), polyurethane, epoxy, polyester, polycarbonate, polystyrene, polyetherimide, polyamide, cycloolefin polymer, cycloolefin copolymer, acrylonitrile butadiene styrene, allyl diglycol carbonate, or silicone.

The apparatus may be configured for wearable use on the user's torso or appendage, e.g. limb, and may comprise an attachment mechanism. The apparatus may be configured for any suitable part of the user's body. For example, the apparatus may be configured as a wrist device that wraps around and can be worn on a user's wrist or other appendage such as the user's foot, or may be configured as a patch that attaches to the skin of a user. The attachment mechanism may comprise one or more of a belt, a snap, a tie, or an adhesive based attachment mechanism.

The apparatus may comprise one or more sensors, where the one or more sensors may be configured to monitor the user and/or the external environment. For instance, the apparatus may comprise a second sensor configured to monitor the user and/or external environment.

In addition, in some embodiments, the support structure further comprises one or more of: a power supply, electronics, and circuitry configured to control the first sensor and any additional sensors in the apparatus. In certain embodiments, the apparatus comprises multiple sections of circuitry, such as a first and a second section of circuitry. The circuitry may be flexible circuitry and may be made integral to the support structure. For instance, in some embodiments, the inner and outer support structure may be laminated to each other to at least partially enclose the circuitry.

In certain embodiments, the apparatus comprises a user actuation section. For instance, in some embodiments, the apparatus may comprise at least one sensor configured to detect user actuation of a part of the apparatus. The sensor signal from the at least one sensor configured to detect user actuation of a part of the apparatus may be configured to control the apparatus.

According to at least some but not necessarily all examples of the disclosure there is provided a method for operating the apparatus, comprising: detecting a user actuation of the apparatus; and controlling operation of the apparatus in dependence on the detected user actuation.

According to at least some but not necessarily all examples of the disclosure there is provided a computer program that, when performed by at least one processor, causes the above method to be performed.

According to at least some but not necessarily all examples of the disclosure there is provided a non-transitory computer readable medium encoded with instructions that, when performed by at least one processor, causes the above method to be performed.

These embodiments of the present invention and other aspects and embodiments of the present invention are described further herein and will become apparent upon review of the following description taken in conjunction with the accompanying drawings.

BRIEF DESCRIPTION OF THE SEVERAL VIEWS OF THE DRAWING(S)

Having thus described example embodiments of the invention in general terms, reference will now be made to the accompanying drawings, which are not necessarily drawn to scale, and wherein:

FIGS. 1A-1C schematically illustrate an example of an apparatus including a ledge spring module according to example embodiments of the present disclosure;

FIGS. 2A-2C schematically illustrate an example of an apparatus including a dome spring module according to example embodiments of the present disclosure;

FIGS. 3A-3C schematically illustrate an example of an apparatus including a spiral spring module according to example embodiments of the present disclosure;

FIGS. 4A-4C schematically illustrate an example of an apparatus including a foam spring module according to example embodiments of the present disclosure;

FIGS. 5A and 5B schematically illustrate an apparatus comprising a support structure and adaptive sensor module according to example embodiments of the present disclosure;

FIG. 6 schematically illustrates an apparatus configured to at least partially enclose the torso or an appendage of a user according to example embodiments of the present disclosure;

FIG. 7 schematically illustrates a circuitry arrangement for an apparatus according to example embodiments of the present disclosure;

FIG. 8 schematically illustrates an apparatus comprising a plurality of sensors according to example embodiments of the present disclosure;

FIG. 9 schematically illustrates an apparatus comprising dual-sensor circuitry according to example embodiments the present disclosure;

DETAILED DESCRIPTION

Figure 1A:
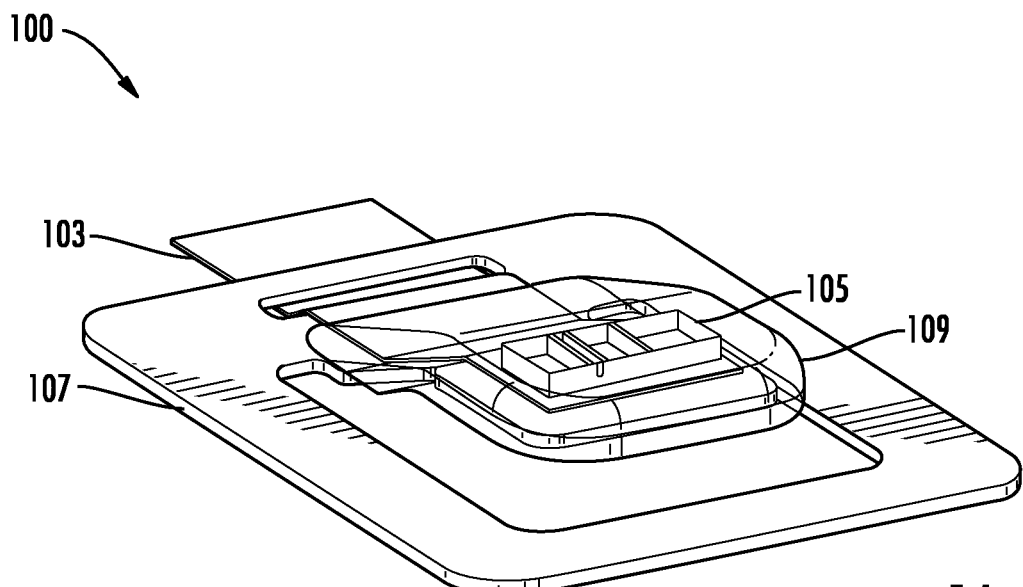

The present invention now will be described more fully hereinafter with reference to the accompanying drawings, in which some, but not all embodiments of the invention is shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

As used in the specification and in the appended claims, the singular forms "a", "an", and "the" include plural referents unless the context clearly indicates otherwise. For example, reference to "a sensor" includes a plurality of such sensors, unless the context clearly indicates otherwise.

As used in the specification and in the appended claims, reference to "on" includes both embodiments in which a component is disposed directly on another component as well as embodiments in which one or more intervening layers or elements are disposed between the components.

As used in the specification and in the appended claims, reference to "user actuation" refers to initiation of any action in the device due to the input of the user. For example, user actuation may refer to user touch or voice control (e.g., by pressing a button, squeezing the device by the user, talking to the device, etc.) that initiates one or more actions in the device (e.g., measuring a physiological condition of the user). As used herein, "user manipulation" refers to physical manipulation of the device by the user that may or may not trigger an action in the device.

In an example embodiment, the incorporation of a sensor disposed on a spring module in a wearable device provides an adaptive device that enables more accurate and reliable physiological measurements. The spring enables the sensor to be decoupled from movements of the device. The spring allows the position of the sensor to be adjusted accordingly such that optimal pressure is applied to the skin of a user. The adaptive wearable device obtains more stable and consistent readings of the physiological conditions of the user, thereby increasing the accuracy and reliability of the data. Further, the device can be made with flexible and/or stretchable material without hindering the reliability and accuracy of the sensor.

In addition, the incorporation of a polymer material with a slightly sticky exterior over the sensor provides a transparent cover allowing for measurement of relevant physiological conditions while also protecting the sensor. The slightly sticky exterior provides friction against the skin of the user to help maintain the location of the sensor against the skin of the user, thereby further increasing the reliability and accuracy of the physiological measurements.

In example embodiments of the present disclosure, the apparatus or wearable device comprises one or more sensors disposed on a spring module. At least the combination of one or more sensors and a spring module may be referred to as an adaptive sensor module. The adaptive sensor module may also include a polymer material and/or circuitry. The spring module allows the apparatus to adapt to movement, whether caused by the user or otherwise, adjust accordingly, and thereby enable the sensor to maintain its relative position. Various configurations of springs, such as those described in detail below, may be used in the adaptive wearable device. In certain embodiments, a polymer material may be disposed over one or more sensors. The polymer material may protect a sensor such that the apparatus has the added benefit of being waterproof, while also allowing for measurement of physiological conditions of the user. The adaptive sensor module is preferably configured such that the sensor faces the skin of the user. Advantageously, such example embodiments provide improved integration of sensors in a wearable device and also provide improved sensing/monitoring of the user. The adaptive wearable device may be positioned on the skin of a user and may be configured to at least partially enclose the torso or an appendage of a user.

Example embodiments of the apparatus according to the present disclosure will now be described with reference to the figures. For instance, various example embodiments of the spring module will be described. Many modifications of the spring module and other components of the example embodiments will come to mind to one skilled in the art to which these inventions pertain having the benefit of the teachings presented in the present descriptions and the associated drawings. Therefore, it is to be understood that the inventions are not to be limited to the specific embodiments disclosed or specific drawings of those embodiments and that modifications and other embodiments are intended to be included within the scope of the appended claims. Similar reference numerals are used in the figures to designate similar features. For clarity, all reference numerals are not necessarily displayed in all figures.

Figure 1B:
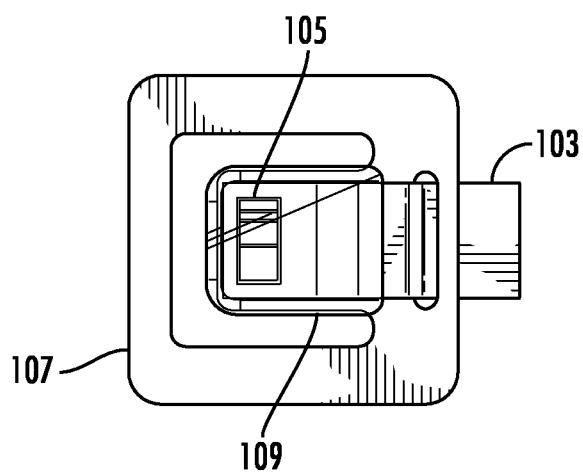
Figure 1C:
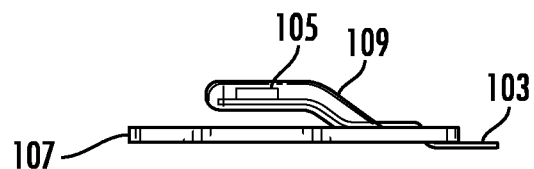

FIGS. 1A, 1B, and 1C schematically illustrate an example of an apparatus including a ledge-type spring module according to example embodiments of the present disclosure. The apparatus 100 illustrated in FIGS. 1A-1C may be referred to as an adaptive sensor module. FIG. 1A provides an isometric view of the apparatus. FIG. 18 provides a top-view of the apparatus, and FIG. 1C provides a side-view of the apparatus. As shown in FIGS. 1A-1C, this embodiment includes a polymer material 109, a first section of flexible circuitry 103, a sensor 105, and a spring module 107. The sensor 105 is disposed on the first section of flexible circuitry 103 which is disposed on the spring module 107. The polymer material 109 is disposed over the sensor 105. In the embodiment illustrated in FIG. 1, the polymer material 109 completely encloses the sensor 105, however, in other embodiments, the polymer material may cover the sensor to various degrees.

In the example embodiment illustrated in FIGS. 1A-1C, the spring module is a ledge-type spring module. As used herein, "ledge-type spring" or "ledge spring" refers to a structure where a portion of the module is elevated above another portion of the module, for instance, as a stair-step allowing for movement of the elevated portion between an elevated position and the position of the other portion of the module. In this example embodiment, the elevated portion (in this case, a "ledge") is adjusted in response to movement of the device and user, such that the sensor, which may be disposed on the ledge, can apply optimal pressure against the skin of the user.

The polymer material may be any transparent resin and preferably has a slightly sticky exterior. For instance, the polymer material may comprise one or more of poly(methyl metacrylate), polyurethane, epoxy, polyester, polycarbonate, polystyrene, polyetherimide, polyamide, cycloolefin polymer, cycloolefin copolymer, acrylonitrile butadiene styrene, allyl diglycol carbonate, or silicone alone or in combination with other materials. Preferably, the polymer material comprises silicone. Silicone resin may provide thermal and photo stability, transparency, enhanced light output efficiency, easy processability, and reduced cost. Silicones are also suitable for high temperature applications as silicones tend to show less yellowing at higher temperatures than plastic, may maintain flexibility over a wide range of temperatures, may be lighter than glass, and may be moisture resistant. MS1002 and MS1003, both by Dow Corning®, are example methyl silicone products for use as the polymer material alone, blended, or in combination with other materials. The polymer material may be injection molded into the desired shape for covering and protecting one or more sensors of the wearable device.

In example embodiments, the polymer material has a slightly sticky exterior to provide friction against the skin of a user and thereby reduce movement of the sensor over the skin. For instance, a signal for an optical heart rate measurement may vary depending on the sensor's relative location to a blood vessel, ambient light leakage to the photodetector, and movement of the sensing element. Vertical displacement, or displacement perpendicular to the surface of the skin by the sensor, may be restricted by an attachment mechanism, e.g. an elastic force forcing the sensor in a direction towards the torso or an appendage. Horizontal displacement, or displacement parallel to/tangential to the surface of the torso or an appendage by the sensor, may by restricted by frictional forces. In the present case, the above described spring module may reduce vertical displacement while the use of a polymer material may reduce horizontal displacement allowing the relative location of the sensor to be maintained and fixed.

The embodiment illustrated in FIGS. 1A-1C includes a first section of flexible circuitry. The first section of flexible circuitry 103 may comprise circuitry mounted thereon, e.g. surface mount device (SMD) components mounted thereon or circuitry printed or integrated thereon. For instance, the first section of flexible circuitry may comprise a flexible wired board, flexible circuit board or flexible printed circuit board. The first section of flexible circuitry may comprise an analog front-end circuitry (AFE), which may have wires to additional circuitry located elsewhere, such as in a second section of flexible circuitry. The additional circuitry may be a controller, such as a microcontroller (MCU), which can store data from the sensor locally and/or send data directly forward through a wireless local connectivity or cellular modem. The additional circuitry may also contain a connector for transferring the data through wired connection, for instance, by real-time streaming or downloading from memory. The same or an alternative connector may also be used for charging the battery, for instance, if a rechargeable battery is used. Wireless charging may also be used as well as non-rechargeable primary cell battery or other power supplies such as various energy harvesting methods. The additional circuitry will be described in greater detail below.

In alternative embodiments, all of the necessary wireless data and power supply may be provided on the spring module without connection to additional circuitry on the device. However, to reduce mass and volume, it may be preferable to have a wired connection from the sensor to the flexible circuitry located on or in immediate proximity to the spring module.

Advantageously, the first section of flexible circuitry is flexible and can be curved so as to conform to any curvature in the apparatus, such as curvature to conform to the shape of the user's torso or appendage to provide a comfortable, wearable apparatus. One or more sensors may be located at any point on the flexible circuitry so long as at least one sensor is disposed along the spring module. A plurality of sensors may be located on the flexible circuitry and in some embodiments, a plurality of sensors may be located on the spring module. The sensors may comprise a plurality of the same type of sensor or differing types of sensors and may monitor the user and/or the external environment. Types of sensors that may be used include, but are not limited to: heart rate, blood pressure, blood oxygen, blood glucose, humidity, temperature, galvanic skin response and skin moisture or other sensors to monitor the user. In addition or instead of the sensors, a device for taking blood samples from or controlling medicine injection to the user's torso or appendage may be provided, such a device being controlled by electronics and circuitry housed in a support structure, which will be described in detail below.

The sensor and the support electronics/control circuitry may be configured to measure physiological measurements such as heart rate (HR) & heart rate variability (HRV) for example using: electrocardiograph (ECG) methods based on direct contact electrodes on the skin or capacitive contact, opto-electrical photoplethysmography (PPG) measurements using a light source, e.g., a light emitting diode (LED) and photodetector (e.g. transistor/diode or a photodiode (PD)) as a receiver against the skin, LED and Photo diode arrays as transmitter-receiver pairs against the skin, a camera as a detector, ultrasonic: Laser Doppler Flowmetry (LDF)/Velocimetry (LDV), radar on the wrist (Nanosecond Pulse Near Field Sensing, NPNS (300 MHz), magnetic methods which utilize Giant-Magneto-Resistance (GMR) to measure Phonocardiographic (PCG) signals, methods utilizing an electrical coil (as a pad of an oscillator), methods utilizing electromechanical film, e.g. Emti(t)-foil, and methods utilizing an acoustic sensor based microphone.

Several artefacts make reliable HR, HRV and peripheral oxygen saturation (SpO2) measurement challenging, such as: movement, breathing and lighting in the environment, for instance, in the case of optical measurements. Various examples of the present disclosure seek to minimize the effect of such artefacts and improve the accuracy of HR, HRV and SpO2 measurements.

In some embodiments, the sensor is a reflective photoplethysmogram (PPG) sensor, which may be configured to measure physiological measurements such as heart rate (HR), heart rate variability (HRV) and peripheral oxygen saturation (SpO2). A reflective photoplethysmogram (PPG) sensor includes one or several LED(s) and photodetector(s). The size of a typical miniaturized PPG sensor is roughly about 3 mm by about 4 mm, but can be made larger or smaller without deviating from the intent of the present disclosure. In some embodiments, the size of the sensor (PPG or other sensor) may be less than about 20 mm by about 20 mm, such as less than about 15 mm by about 15 mm, less than about 10 mm by about 10 mm, less than about 5 mm by about 5 mm, or less than about 3 mm by about 3 mm. The size of the PPG-sensor and other possible electrical components mounted on the spring (e.g. the AFE) may influence the size of the spring module. There are several options for spring material and geometry. For instance, the spring module and flexible circuitry may comprise any suitable material such as metal and plastic. For instance, the spring module and flexible circuitry may comprise stainless steel, polyamide, carbon fiber based materials or combinations thereof. The height of the spring can also be varied. For instance, a ledge-type spring module may have a frame about 20 mm×about 20 mm and height of about 2 mm. In some embodiments, the size of the spring module (ledge-type, dome-type, spiral-type, foam-type, or otherwise) may be less than about 50 mm by about 50 mm, such as less than about 40 mm by about 40 mm, less than about 30 mm by about 30 mm, less than about 20 mm by about 20 mm, or less than about 10 mm by about 10 mm. The spring module (ledge-type, dome-type, spiral-type, foam-type, or otherwise) may have a height of less than about 10 mm, such as less than about 9 mm, 8 mm, 7 mm, 6 mm, 5 mm, 4 mm, 3 mm, 2 mm, or 1 mm. Dimensions of the components of the adaptive wearable device can vary depending on the electrical components, spring material, device attachment location, strap type, etc. for the embodiment without deviating from the intent of the present disclosure.

The sensor may comprise: electrodes, functional material that converts physical properties into an electrical signal, or other electronics e.g. transistors and passives, and may be printed onto or integrated into the first section of flexible circuitry. In certain embodiments, at least one sensor is disposed towards an inwardly facing side of the apparatus, such as facing the side of the apparatus to be disposed adjacent to the skin of a user.

Figure 2A:
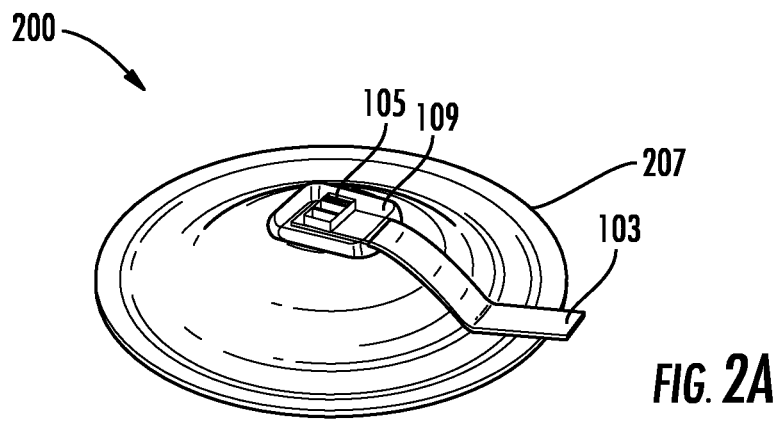
Figure 2B:
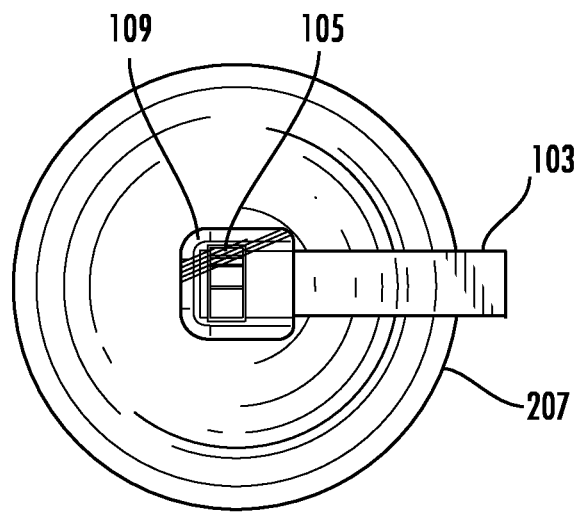
Figure 2C:
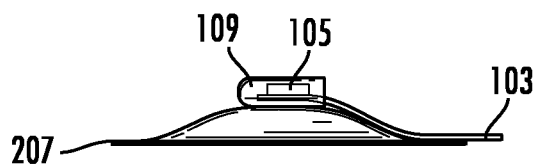

FIGS. 2A, 2B, and 2C schematically illustrate an example of an apparatus including a dome-type spring module according to example embodiments of the present disclosure. The apparatus 200 illustrated in FIGS. 2A-2C may be referred to as an adaptive sensor module. FIG. 2A provides an isometric view of the apparatus. FIG. 2B provides a top-view of the apparatus, and FIG. 2C provides a side-view of the apparatus. As shown in FIGS. 2A-2C, the embodiment includes a polymer material 109, a first section of flexible circuitry 103, a sensor 105, and a spring module 207. The sensor 105 is disposed on the first section of flexible circuitry 103, which is disposed on the spring module 207. The polymer material 109 is disposed over the sensor 105. In the embodiment illustrated in FIGS. 2A-2C, the polymer material 109 completely encloses the sensor 105, however, in other embodiments, the polymer material may cover the sensor to various degrees.

In the embodiment illustrated in FIGS. 2A-2C, the spring module is a dome-type spring module. As used herein, "dome-type spring" or "dome spring" refers to a convex structure where a portion of the module is elevated above the other portion of the module in a convex shape allowing for movement of the elevated portion between an elevated position and the position of the other portion of the module. The elevated portion (in this case, a "dome") is adjusted in response to movement of the device and/or user such that the sensor, which may be disposed on the dome, can apply optimal pressure against the skin of the user.

Figure 3A:
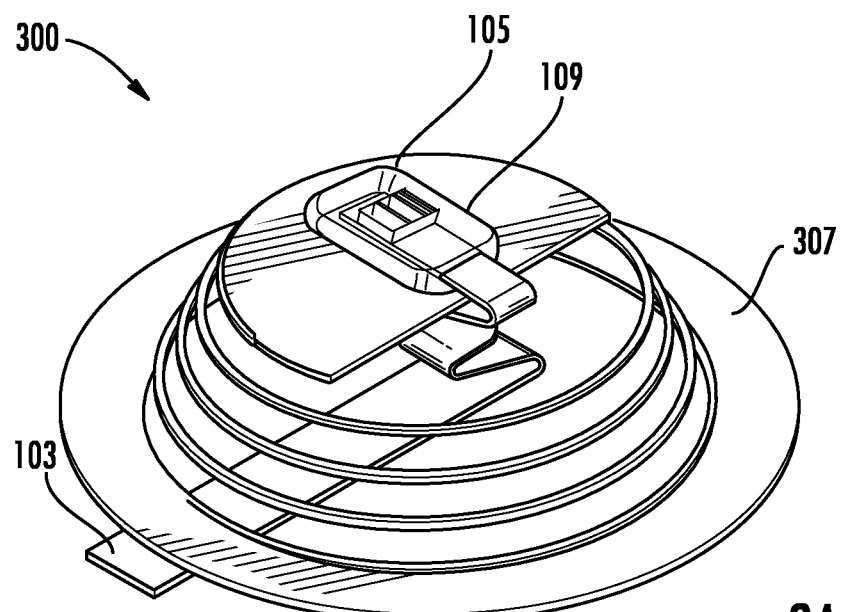
Figure 3B:
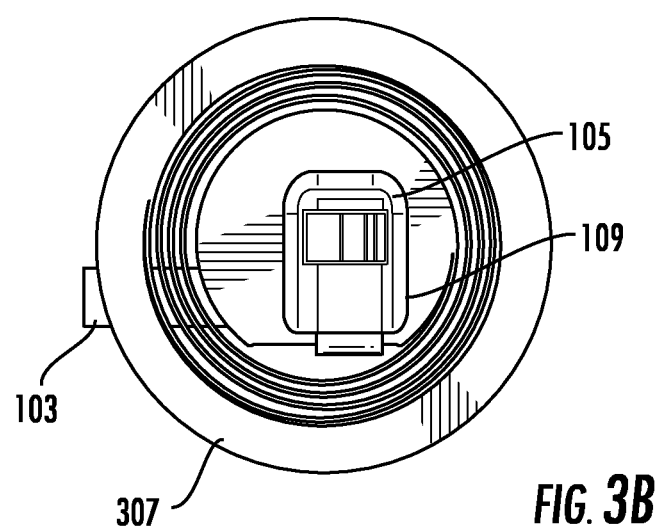
Figure 3C:
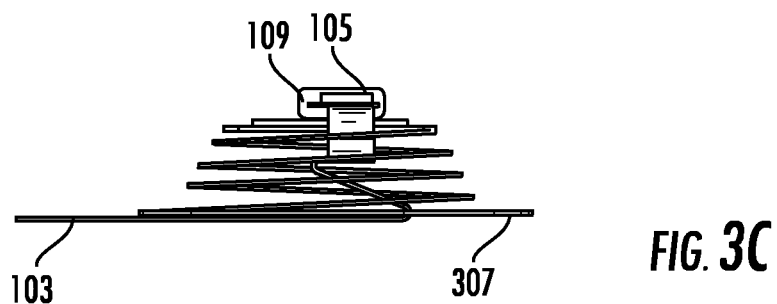

FIGS. 3A, 3B, and 3C schematically illustrate an example of an apparatus including a spiral-type spring module according to example embodiments of the present disclosure. The apparatus 300 illustrated in FIGS. 3A-3C may be referred to as an adaptive sensor module. FIG. 3A provides an isometric view of the apparatus. FIG. 3B provides a top-view of the apparatus, and FIG. 3C provides a side-view of the apparatus. As shown in FIGS. 3A-3C, the embodiment includes a polymer material 109, a first section of flexible circuitry 103, a sensor 105, and a spring module 307. The sensor 105 is disposed on the first section of flexible circuitry 103, which is disposed on the spring module 307. The polymer material 109 is disposed over the sensor 105. In the embodiment illustrated in FIGS. 3A-3C, the polymer material 109 completely encloses the sensor 105, however, in other embodiments, the polymer material may cover the sensor to various degrees. In addition, as shown in FIGS. 3A-3C, the first section of flexible circuitry 103 can be configured such that the spring module is not limited in movement in the x, y, and z directions. That is, the first section of flexible circuitry may be disposed on the spring module such that the spring module and the sensor disposed on the module can move in all three directions—x, y, and z.

In the embodiment illustrated in FIGS. 3A-3C, the spring module is a spiral-type spring module. As used herein, "spiral-type" refers to a spiral (a curve which emanates from a central point, getting progressively farther away as it revolves around the point) structure where a portion of the module is elevated above the other portion of the module allowing for movement of the elevated portion between an elevated position and the position of the other portion of the module. The elevated portion (in this case, a "spiral") is adjusted in response to movement of the device and user such that the sensor, which may be disposed on the spiral, can apply optimal pressure against the skin of the user.

Figure 4A:
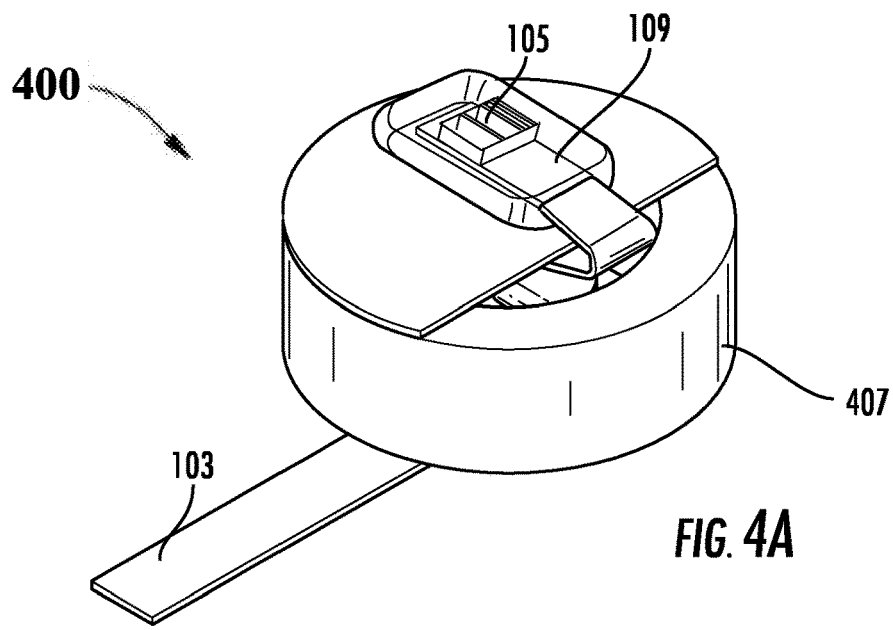
Figure 4B:
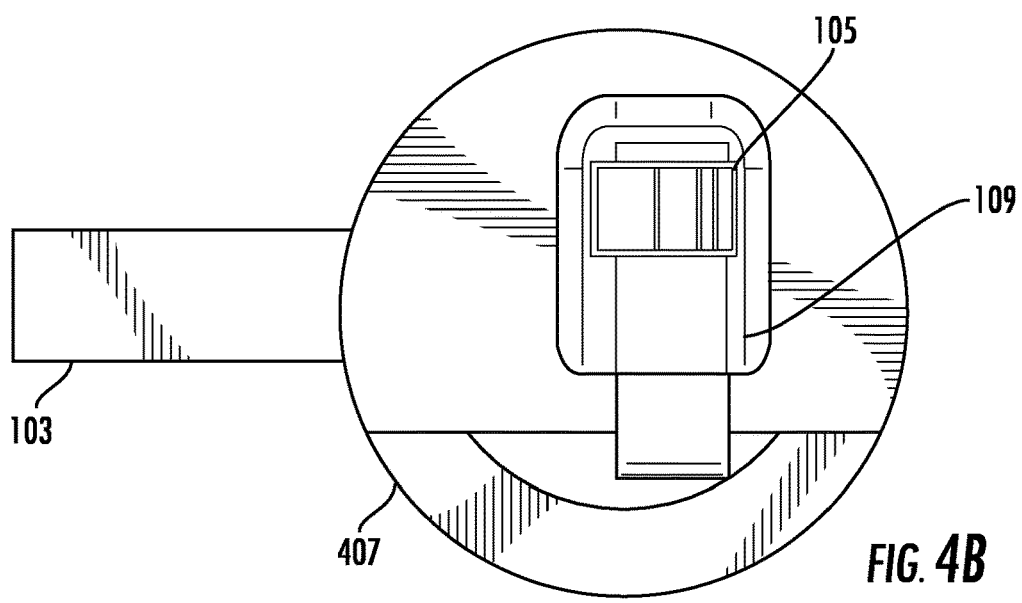
Figure 4C:
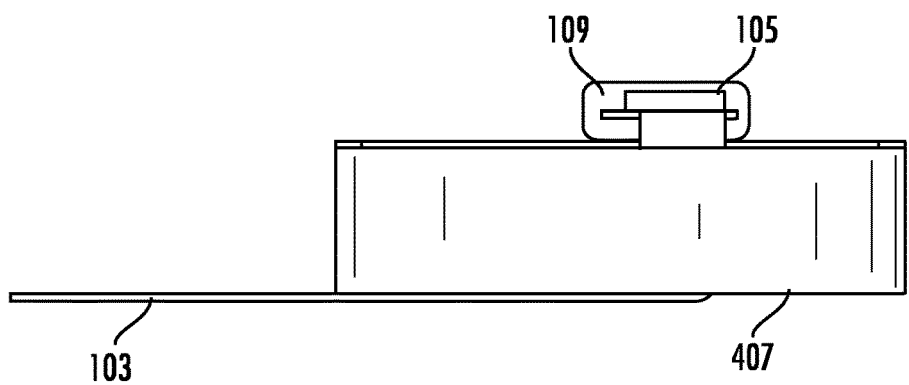

FIGS. 4A, 4B, and 4C schematically illustrate an example of an apparatus including a foam-type spring module according to example embodiments of the present disclosure. The apparatus 400 illustrated in FIGS. 4A-4C may be referred to as an adaptive sensor module. FIG. 4A provides an isometric view of the apparatus. FIG. 4B provides a top-view of the apparatus, and FIG. 4C provides a side-view of the apparatus. As shown in FIGS. 4A-4C, the embodiment includes a polymer material 109, a first section of flexible circuitry 103, a sensor 105, and a spring module 407. The sensor 105 is disposed on the first section of flexible circuitry 103, which is disposed on the spring module 407. The polymer material 109 is disposed over the sensor 105. In the embodiment illustrated in FIGS. 4A-4C, the polymer material 109 completely encloses the sensor 105, however, in other embodiments, the polymer material may cover the sensor to various degrees.

In the embodiment illustrated in FIGS. 4A-4C, the spring module is a foam-type spring module. As used herein, "foam-type" refers to the use of a foam in the module that responds to movement of the device and adjusts or absorbs the movement such that the sensor, which may be disposed on the foam, can apply optimal pressure against the skin of the user.

FIGS. 1A-4C illustrate various embodiments of the adaptive sensor module particularly highlighting various spring modules that may be used in the adaptive sensor module. The adaptive sensor module may be disposed on a substrate, such as a support structure, to increase the stability of the apparatus, change the shape and form of the footprint of the apparatus, and/or incorporate an attachment mechanism such that the adaptive sensor module may be attached to a user for monitoring. For instance, the adaptive sensor module may be disposed on a support structure in the shape of a patch, band, belt, or strap that can be attached to a user. In some embodiments, the adaptive sensor module may be provided in a module. As used here "module" refers to a unit or apparatus that excludes certain parts or components that would be added by an end manufacturer or a user.

Figure 5A:
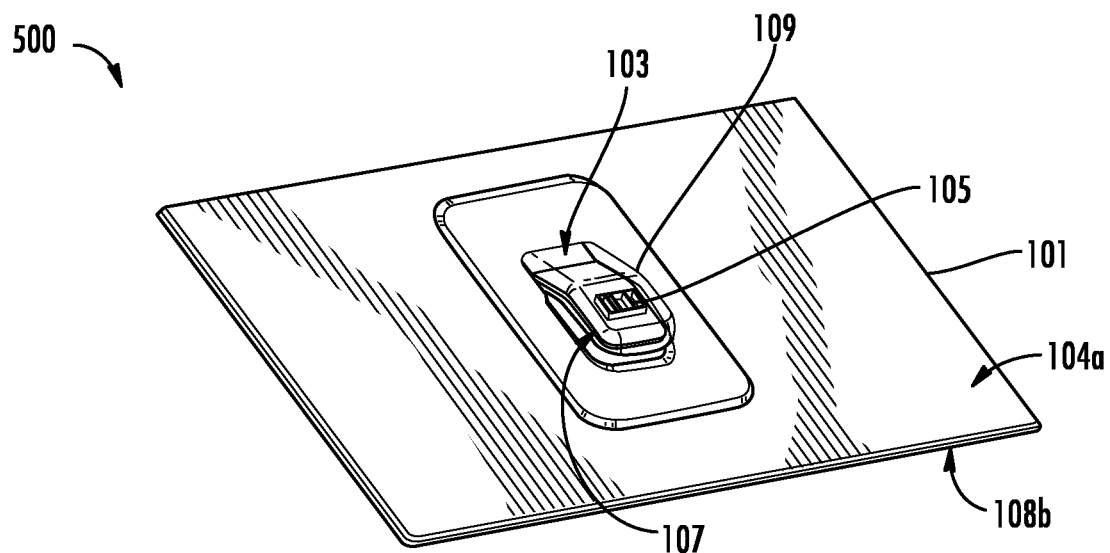
Figure 5B:
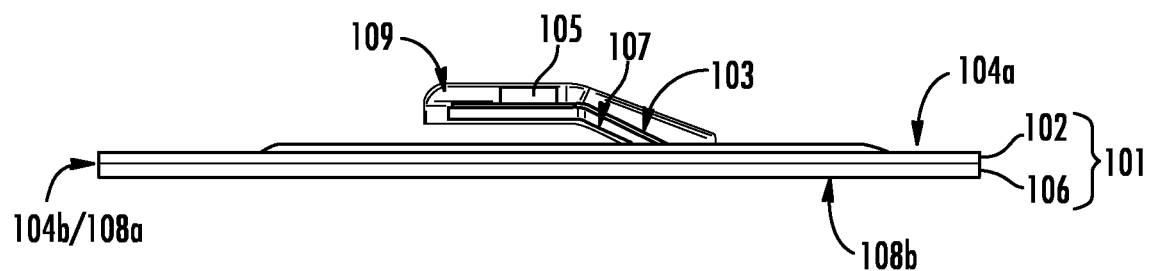

FIGS. 5A and 5B schematically illustrate an apparatus 500 comprising a support structure and adaptive sensor module according to example embodiments of the present disclosure. FIG. 5A provides an isometric view of the apparatus, and FIG. 5B provides a side-view of the apparatus. In the embodiment illustrated in FIGS. 5A-5B, the first section of flexible circuitry 103 and sensor 105 are disposed on the spring module 107 and the polymer material 109 is disposed over the sensor 105, The apparatus further comprises a support structure 101, which in this example embodiment, comprises an inner support layer 102 and an outer support layer 106. The first section of flexible circuitry 103, the sensor 105, the spring module 107, and the polymer material 109 are at least partially enclosed between the inner support layer 102 and the outer support layer 106. In the embodiment illustrated in FIG. 5A-5B, the inner support layer 102 and outer support layer 106 are laminated together to at least partially enclose the sensor 105, first section of flexible circuitry 103, spring module 107, and polymer material 109 between the two support layers. In the embodiment illustrated in FIGS. 5A-5B, the inner support layer 102 has an opening exposing the polymer material 109 to the environment. When the adaptive wearable device is attached to a user, the opening in the inner support layer 102 allows the polymer material 109 to be exposed to and immediately adjacent to the skin of the user.

The support structure provides an overarching framework for the apparatus and may comprise mechanical support for components of the apparatus, e.g. a user interface, electrical components, control circuitry and power supply for the apparatus, in addition to supporting the first section of flexible circuitry, the spring module, and the sensor. The support structure may be: a mechanical architecture, support means, support member, a frame, a chassis or a skeleton structure which forms the back bone of the apparatus. In some embodiments, the support structure is configured to at least partially enclose, envelope or wrap around a user's torso or appendage, e.g. a user's wrist, such that the apparatus may be worn by the user around the user's torso or appendage, for example in the form of a belt, band, bracelet or strap for wearing on a wrist or other body location. In other embodiments, the support structure may be in the form of a patch or similar structure that does not at least partially enclose the torso or an appendage of a user and instead is attached by adhesive or similar means to a portion of a user's body (e.g., the torso or an appendage). The support structure may be curved, having a curvilinear cross section substantially of a generally oval/circular/band like shape. In some embodiments discussed below, the apparatus has a bracelet/band like form that does not form a closed loop (a "C" shaped cross section).

The support structure, such as the inner and outer support layers, may comprise any suitable material and preferably is a flexible and stretchable substrate. The support structure may be made of flexible and/or elastic material that allows for bending and shaping of the structure around the user's torso or appendage, such as cloth or bandage material, which may also be breathable i.e. allow humidity to travel through the structure. For instance, the support structure may comprise natural or synthetic materials based on leather, rubber, fabrics, and textiles. The support structure may comprise metal or plastic. The inner and outer support layers may be the same or different and may comprise a mixture or composite of various materials. The support structure may also comprise more ridged components.

In the embodiment illustrated in FIGS. 5A-5B, the support structure 101 comprises an inner support layer 102 with an inner side 104a and an outer side 104b. The inner side 104a of the inner support layer 102 corresponds to an inner side of the support structure. The support structure 101 also includes an outer support layer 106 with an inner side 108a and an outer side 108b. The outer side 108b of the outer support layer 106 corresponds to an outer side of the support structure. When the apparatus is worn by a user, the inner support layer 102 corresponds to a side which is proximal to the user and the outer support layer 106 corresponds to a side which is distal from the user. The inner side 104a of the inner support layer 102 may be immediately adjacent to the user's skin. In other embodiments, the support structure may comprise additional layers between the inner support layer and outer support layer. In certain other embodiments, the support structure comprises a single layer with the adaptive sensor module disposed on the layer such that the sensor and/or polymer material is disposed proximal to the user's skin when worn.

In the embodiment illustrated in FIGS. 5A-5B, the first section of flexible circuitry 103 is disposed on the spring module 107, which is disposed on the outer support layer 106. In some embodiments, the first section of flexible circuitry may extend along a substantial portion of the spring module and may extend beyond the spring module. For instance, the first section of flexible circuitry may extend along the entirety of the support structure. In other embodiments, the first section of flexible circuitry may extend to cover at least a portion or full length of the support structure, while in other embodiments, the first section of flexible circuitry may be located on the support structure but not on the spring module. As will be discussed in greater detail below, the support structure may comprise additional electronics, circuitry and a power supply for controlling one or more sensors.

Figure 6:
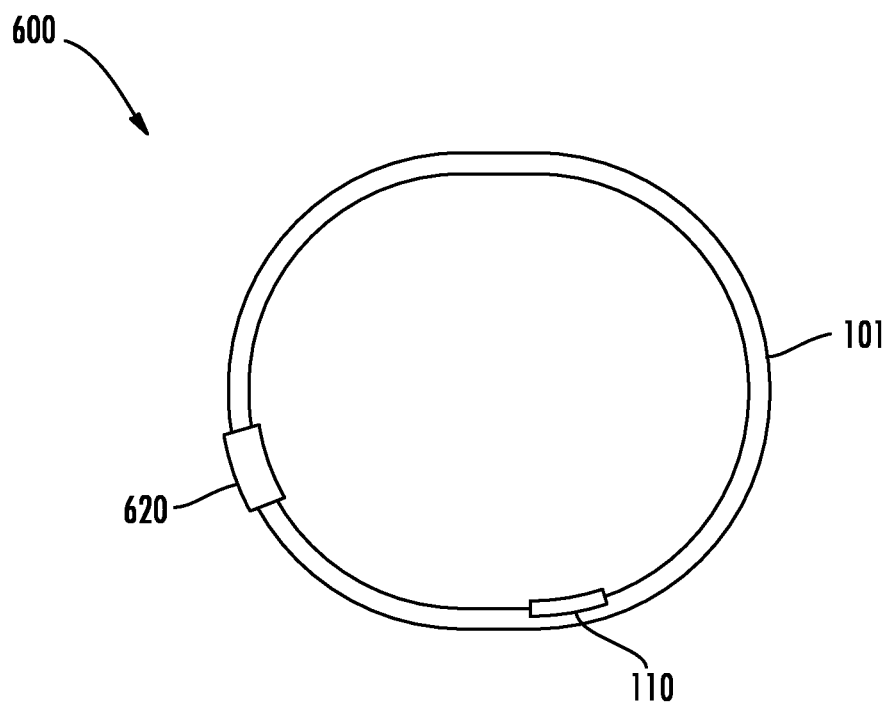

FIG. 6 schematically illustrates an apparatus configured to at least partially enclose the torso or an appendage of a user according to example embodiments of the present disclosure. The apparatus 600 illustrated in FIG. 6 comprises a support structure 101 and an adaptive sensor module 110. The adaptive sensor module comprises one or more sensors and one or more spring modules where at least one sensor is located on a spring module. The adaptive sensor module may additionally comprise a polymer material disposed over one or more sensors. The adaptive sensor module is preferably positioned to be immediately proximal to the skin of a user. The adaptive sensor module may also comprise circuitry connected to the sensor or the circuitry may be located outside of the adaptive sensor module and connected by wire to the sensor. The support structure may comprise additional electronics, circuitry and power supply for supporting one or more sensors of the adaptive sensor module. The additional circuitry may be located anywhere on the support structure and may communicate with the sensor by wire or wirelessly.

The apparatus illustrated in FIG. 6 includes an attachment mechanism 620 that allows the apparatus to at least partially enclose the torso or an appendage of a user. Any suitable attachment mechanism may be employed to temporarily, semi-permanently and permanently attach the apparatus to the user, whether partially enclosing the torso or an appendage of the user or not. Such mechanisms may include, for example: belts, bands, bracelets, straps (e.g., to be tied), bandages, stickers, tapes, plaster, fastening means (e.g., snaps), adhesive means, as well as tattoos. The mechanism may be: adjustable, stretchable and conformable to a user to ensure an appropriate level of tightness of fit. For instance, the attachment mechanism may include a fastening device to secure and tighten the apparatus around a user's appendage or torso. For example, a hook and loop based fastening strap may be used in this regard. Alternatively, other fastening and/or clasping means may be used.

The support structure may be configured such that it has portions of varying rigidity. The support structure may have rigid portions, for instance, to support circuitry, while, in other example embodiments, the support structure may be substantially flexible. For instance, the incorporation of the spring module enables the support structure to be flexible as well as stretchable without the need for large rigid portions while still obtaining reliable and consistent readings of the user. The apparatus is bendable and can provide a more comfortable device for the user to wear.

The support structure may have flexible portions that may be bent upon user manipulation, e.g. a user squeezing the apparatus between thumb and forefinger, so as to enable movement of the flexible portions of the support structure. The bending of the support structure by the user allows the user to conform the shape of the support structure to the portion of the body to which the device will be adjacent, e.g., the torso or appendage. Such flexibility may improve user comfort. The support structure may comprise rigid sections, which may be used to house electrical components and hardware mounted therein, to protect delicate circuitry and main electronic components, such as control circuitry of the apparatus. The rigid, bendable, and flexible portions of the support structure could be achieved by any suitable means, e.g. providing relatively thicker and thinner portions of the support structure or making such portions of the support structure from materials having the appropriate mechanical characteristics. Alternatively, a mechanism could be provided to enable bending, such as a hinge.

The apparatus may be provided with means configured to withstand a degree of bending applied by the user to the support structure. Means configured to withstand a degree of bending of the apparatus could relate to the selection of materials for parts of the apparatus, e.g. resilient materials, or the structure of the apparatus, e.g. sections of reduced width to permit a degree of bending. Means configured to limit a degree of bending of the apparatus could also be provided. For example, rigid sections of the support structure could be provided with a protruding member configured to mate/engage with a corresponding recession in a flexible section such that bending of the apparatus causes the protrusion to enter into and engage with the recession. A gap may be provided between the recession and the protrusion to permit a degree of movement/bending of the apparatus, but limit the degree of bending e.g. when the protrusion fully engages with and abuts against recession thereby preventing any further movement and bending.

Figure 7:
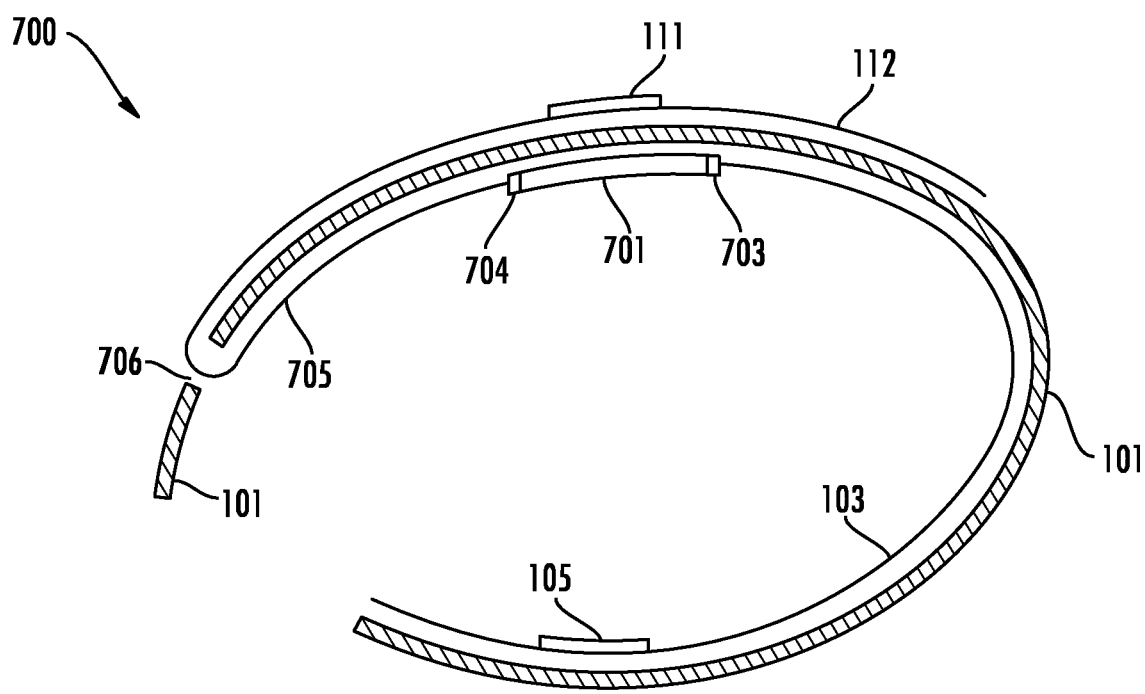

FIG. 7 schematically illustrates circuitry according to example embodiments of the present disclosure comprising multiple sensors and a first and second section of flexible circuitry. In the embodiment of FIG. 7, the apparatus 700 includes a first section of flexible circuitry 103, a sensor 105 (e.g., a first sensor), and a support structure 101. The spring module and/or polymer material is not illustrated in this figure. However, one or more of these elements may be included in this example embodiment. The first flexible circuitry section 103 and first sensor 105 may be referred to as an inner sensor foil.

The example embodiment also includes an additional sensor (e.g., a second sensor) 111 disposed on the support structure 101. In the embodiment illustrated in FIG. 7, the second sensor 111 is directly across from the first sensor 105.

In other embodiments, the second sensor may be positioned anywhere on the support structure and may be flexible/curved so as to conform to the shape of the support structure and the user's torso or appendage. Similarly, the first sensor 105 may not be limited in its location within the apparatus. Instead, the sensor 105 can be flexible/curved so as to conform to the shape of the support structure and the user's torso or appendage and can be disposed along with the spring module anywhere along the support structure 101. The sensor 105 can be in direct physical contact with, or immediately proximal to, the user's skin/wrist.

In the embodiment illustrated in FIG. 7, a second section of flexible circuitry 112 is provided on the support structure 101. The second section of flexible circuitry 112 is coupled to and supported by the support structure 101. In certain embodiments, the second section of flexible circuitry may extend around a portion of the support structure, while in some embodiments, the second section of flexible circuitry may cover the entirety of the support structure. The second flexible circuitry section 112 and second sensor 111 may be referred to as an outer sensor foil.

The inner and outer sensor foils can be coupled to the support structure via any suitable means, for example adhered by double sided adhesive tape. In example embodiments, at least the inner sensor foil is coupled to the support structure by being disposed between two layers of the support structure. In some embodiments, the layers are laminated together to at least partially enclose the inner sensor foil between the two layers of the support structure. The outer sensor foil may be coupled to the support structure in a similar fashion.

The second section of flexible circuitry may comprise circuitry mounted thereon, e.g. SMD components mounted thereon or circuitry printed or integrated thereon, such as at least a second sensor or an array of sensors. The second sensor may be outwardly disposed on the apparatus so as to be exposed to the external environment (directly exposed or covered by a protective layer) or may be disposed inward to be exposed to the skin of a user. When exposed to the external environment, the second sensor may monitor the external environment, e.g. measure and detect conditions external of the apparatus or other sensors to monitor an external environment (cf. monitoring the user).

The second sensor or array of sensors may be configured to extend or be disposed along a substantial portion of the second section of flexible circuitry or may be adjacent to the second section of flexible circuitry. The second sensor or array of sensors may comprise a plurality of the same type of sensor or differing types of sensors. For instance, the second sensor or array of sensors may monitor one or more of the following: humidity, temperature, touch, strain, stretch, bend, compression, as well as contortion or user manipulation of the apparatus. A strain sensor may be used to detect user manipulation of a part of the apparatus. For instance, the strain sensor may detect squeezing or flexing of the apparatus. A signal from such a sensor, which may be indicative of user actuation of the apparatus, could be used for a user input or user interface command. The signal may be provided to a controller circuitry mounted on the support structure and used as an input command for a user interface or to control the apparatus in dependence on detection of user actuation. Advantageously, certain examples of the present disclosure provide a wrist device comprising at least a first sensor optimally arranged to monitor a user of the apparatus, and at least a second sensor optimally arranged to monitor an external environment and/or user actuation.

FIG. 7 illustrates an embodiment of the present disclosure where a first section of flexible circuitry 103 is electrically connected to intermediate circuitry 701 via electrical connector 703. The second flexible circuitry section 112 is electrically connected to the circuitry 701 via a portion of second flexible circuitry 705 (which passes through an aperture, slot or opening 706 in the support structure, such that the portion of the second flexible circuitry 705 is disposed on the inner side of the support structure) and electrical connector 704, such that the circuitry 701 is interposed between the first and second flexible circuits. The circuitry 701 may be inherently rigid, e.g., a rigid: circuit board, printed circuit board or printed wired board, or may be flexible, e.g., a flexible: circuit board, printed circuit board or printed wired board. Alternatively, instead of having a rigid planar flat substrate, the circuitry could be rigidly supported by a rigid planar flat surface of the support structure. Advantageously, providing a rigid flat/planar circuitry section may facilitate the mounting and integration of electrical hardware and components, such as a controller as discussed with reference to FIG. 10 or other circuitry, components, devices and sensors (e.g. accelerometers, GPS receivers), not suitable for printing on flexible circuitry.

The first and second sections of flexible circuitry could correspond to separate and/or different flexible circuits. The material of the flexible substrate of the first section of flexible circuitry may be different to the material of the flexible substrate of the second section of flexible circuitry. Alternatively, the first and second sections of flexible circuitry along with an intermediate circuitry section could be integrally formed as a single unit, with the intermediate circuitry section (e.g., 701 in FIG. 7) being provided by rigid support from the support structure or by the provision of a rigid substrate. The rigid support may be in the form of a flat planar rigid support. In such an embodiment, where the first and second sections of flexible circuitry are integrally formed as a single unit with intermediate circuitry, the connectors (e.g., 703 and 704 of FIG. 7) may not be required.

In a further example of the present disclosure, the first and second sections of flexible circuitry may correspond to first and second sides of the same single flexible circuit, which may be appropriately wrapped around the support structure so as to have a first section disposed towards an inner side and a second section disposed towards an outer side of the support structure.

Advantageously, placing intermediate circuitry, such as 701 of FIG. 7, on an inner side of the support structure helps protect the circuitry and the main electrical components of the apparatus from the external environment. However, in an alternative example, the intermediate circuitry may be provided on the outer side of the support structure, such that an equivalent aperture (e.g., aperture 706) and wrap around arrangement would be provided for the first section of flexible circuitry to enable the first section of flexible circuitry, disposed on an inner side of the support structure, to be electrically connected to intermediate circuitry disposed on the outer side of the support structure.

In yet a further example, the support member may be provided with an aperture/window within which the intermediate circuitry is disposed and the first section of flexible circuitry attached thereto may be bent, folded or passed through the aperture to the inner side of the support structure whilst the second section of flexible circuitry attached to the intermediate circuitry may be bent, folded or passed through the aperture to the outer side of the support structure.

Figure 8:
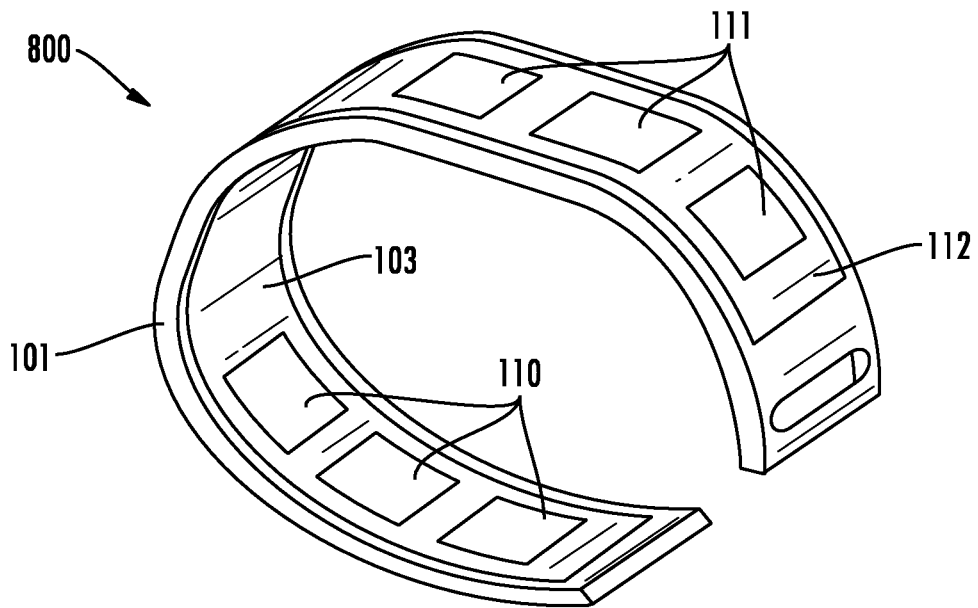

FIG. 8 schematically illustrates an apparatus comprising a plurality of sensors according to example embodiments of the present disclosure. In the embodiment illustrated in FIG. 8, the apparatus 800 comprises a plurality of sensors. The apparatus 800 comprises a plurality of adaptive sensor modules 110 disposed on the inner side of the support structure 101 and a plurality of second sensors 111 disposed on the outer side of the support structure 101. The apparatus includes a first section of flexible circuitry 103 and a second section of flexible circuitry 112. In certain embodiments, the apparatus comprises an array of integrated/printed sensors thereon so as to substantially cover the inner side of the support structure and outer side of the support structure thereby increasing the sensing surface area of the device. One or more of the sensors may be configured to monitor a user of the apparatus via contact with a user's torso or appendage, e.g. wrist, (e.g., direct physical contact or contact through a polymer material) so as to take a physiological measurement of the user. One or more sensors may be part of an adaptive sensor module. One or more of the sensors may be configured to monitor an external environment. Still further, one or more sensors may be configured to monitor user actuation of the device. The sensors may have one or more additional protective layers besides the polymer material.

While not illustrated in FIG. 8, circuitry may be disposed along with the second sensors on the support structure 101 as a collective unit or with each individual sensor. As described above the adaptive sensor module may comprise circuitry for each enclosed sensor.

Electrical components and electrical hardware, such as a controller, processor and memory, may be mounted and integrated in the support structure. The support structure may comprise a rigid/flat portion for supporting electronic components, such as interface, power supply, and electronics/circuitry for controlling one or more sensors. The interface may provide power as well as control signals to the plurality of sensors. Also, the interface may receive sensor measurements from the sensors. The interface may provide a wired connection (e.g. via cables or flexible circuitry such as a flexible circuit board (FCB)), a wireless connection (e.g. via radio frequency, NEC, infrared (IR) or optical based wireless communication) or alternatively the interface may be via galvanic contacts such as sliding galvanic spring connectors for transferring data and energy to the sensors.

Figure 9:
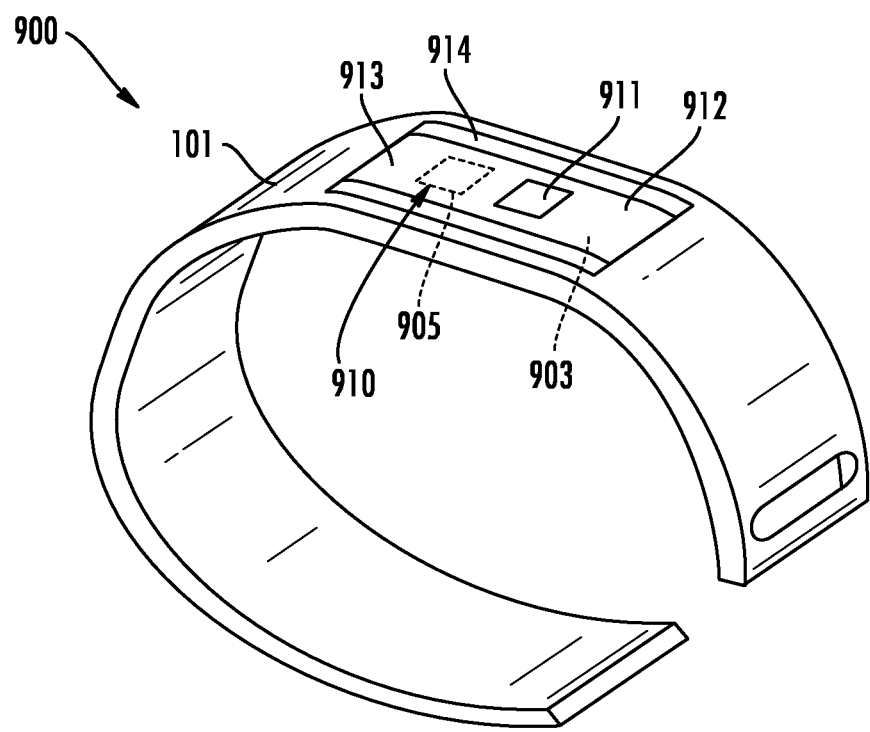

FIG. 9 illustrates an additional example of an apparatus 900 according to example embodiments of the present disclosure. In the embodiment illustrated in FIG. 9, the apparatus comprises multiple sensors. The apparatus 900 comprises a support structure 101 having an aperture or window there through 914. The aperture is configured such that flexible circuitry can be disposed therein.

In this example, the first and second sections of flexible circuitry 903 and 912 correspond to first and second major surfaces/sides of the same single flexible circuitry or substrate 913 which is disposed and mounted within the aperture 914. In effect, a double sided flexible circuitry 913 is provided with first flexible circuitry section 903 on one side disposed towards an inwards direction and second flexible circuitry section 912 on the other side disposed towards an outward direction. The apparatus may comprise one or more adaptive sensor modules 910 including one or more first sensor(s) 905 (shown in outline) mounted on a first under side of the double sided flexible circuitry 913 and disposed towards an inner side of the support structure. One or more second sensor(s) 911 may be mounted/printed on an opposing second upper side of the double sided flexible circuitry 913 and disposed towards an outer side of the support structure.

The aperture, window or opening 914 could be provided through the support structure 101 such that the first sensor on the first side is exposed to the user's torso or appendage. Also, the first sensor may be configured to monitor the user. The second sensor on the second side may be exposed to the external environment and the second sensor may be configured to monitor the external environment and/or monitor user actuation.

Although not shown, it is to be appreciated that one or more further adaptive sensor modules may additionally be provided which extend beyond the aperture and are disposed on the inner side of the support structure. Similarly, one or more further second sections of flexible circuitry (with one or more second sensor(s) thereon) could be provided on the outer side of the support structure. In a yet further embodiment, the double sided circuitry/substrate 913 may be rigid.

Figure 10:
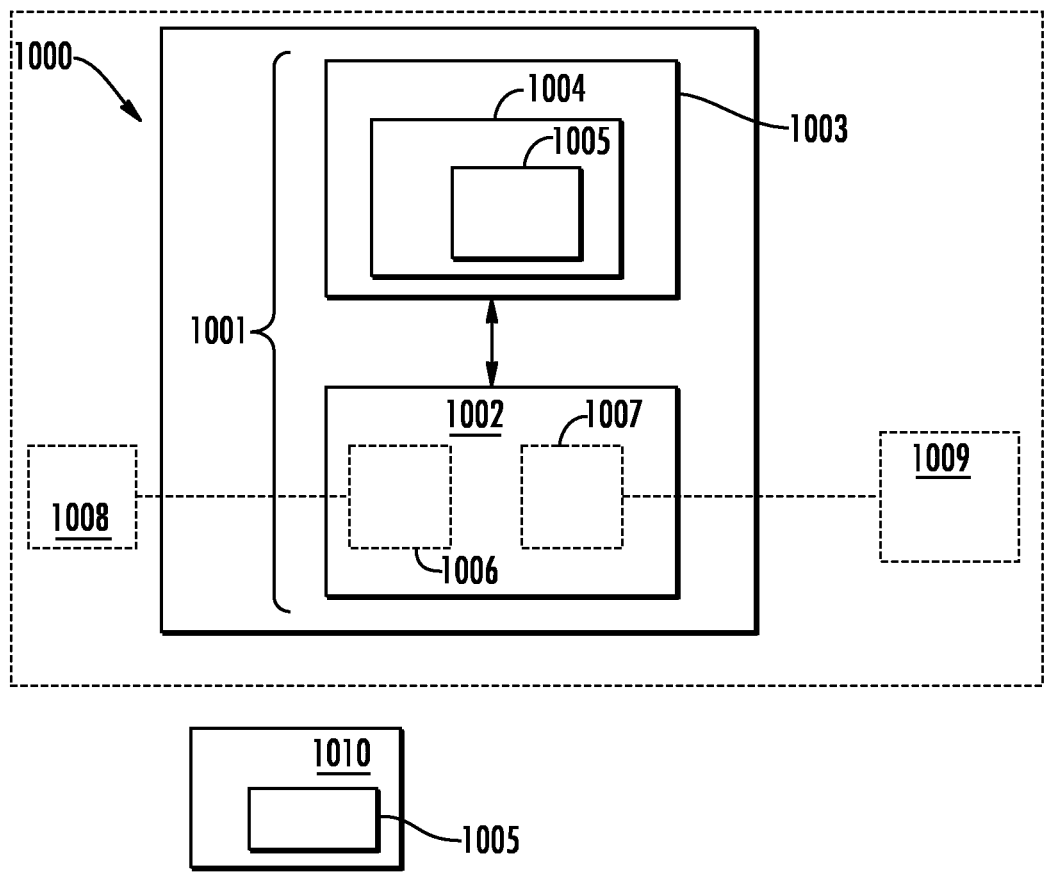
FIG. 10 illustrates an example of a controller for an apparatus according to example embodiments of the present disclosure.

FIG. 10 schematically illustrates an example of a controller for an apparatus according to example embodiments of the present disclosure. The controller controls the sensors and/or other functionality of components in the apparatus according to the present disclosure. The controller may be integrated in the support structure.

Implementation of the controller 1000 can be in hardware alone (e.g. processing circuitry 1001 comprising one or more processors 1002 and memory circuitry comprising one or more memory elements 1003), have certain aspects in software including firmware alone or can be a combination of hardware and software (including firmware).

The controller 1000 may be implemented using instructions 1005 that enable hardware functionality, for example, by using executable computer program instructions 1005 in a general-purpose or special-purpose processor that may be stored on a computer readable storage medium 1003 (e.g. memory) or carried by a signal carrier, to be performed by such a processor.

In the illustrated example, the controller 1000 is provided by a processor 1002 and memory 1003. Although a single processor and a single memory are illustrated in other implementations there may be multiple processors and/or there may be multiple memories some or all of which may be integrated/removable and/or may provide permanent/semi-permanent/dynamic/cached storage. In the embodiment illustrated in FIG. 10, the processor 1002 is configured to read from and write to the memory 1003.

The processor 1002 may also comprise an input interface 1006 via which data, such as sensor signals and/or commands, are input to the processor 1002 from at least one input device 1008 (e.g., first and second sensors) and an output interface 1007 via which data and/or commands are output by the processor 1002 to output device 1009. The output device may comprise: a transceiver via which data may be wirelessly communicated to other devices, an audio output device such as a speaker a visual output device such as a display, lights or other visual indication means, or a haptic output device such as a vibrator.

In the embodiment of FIG. 10, the memory 1003 stores a computer program 1004 comprising computer program instructions 1005 that control the operation of the apparatus when loaded into the processor 1002. The computer program instructions may provide the logic and routines that enable the apparatus to effect functionality, such as controlling the sensors, user input/output, wireless communication and also the method 1100 discussed below with respect to FIG. 11.

The computer program instructions 1005 may arrive at the controller 1000 via any suitable delivery mechanism. The delivery mechanism may be, for example, a non-transitory computer-readable storage medium 1010, a computer program product, a memory device, a record medium such as a compact disc read-only memory or digital versatile disc, or an article of manufacture that tangibly embodies the computer program. The delivery mechanism may be a signal configured to reliably transfer the computer program.

Figure 11:
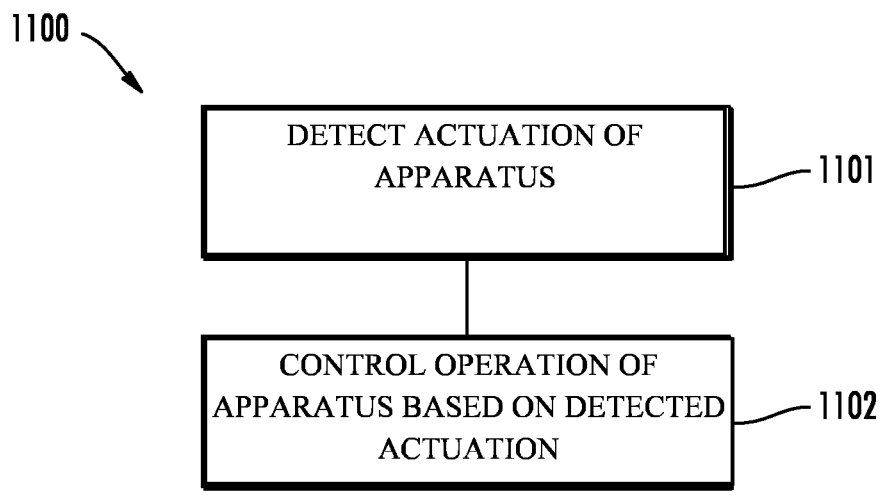
FIG. 11 illustrates a method according to example embodiments of the present disclosure.

FIG. 11 illustrates a method according to embodiments of the present disclosure. In block 1101, user actuation of the wearable device, or apparatus, is detected. For instance, in some embodiments, a second section of flexible circuitry located on the wearable device could comprise a strain sensor printed thereon configured to detect bending and relative movement of the support structure. Such an arrangement would be able to recognize user actuation of the support structure, e.g. a user squeezing the apparatus between his/her thumb and forefinger.

In block 1102, operation of the apparatus is controlled in dependence on the detected actuation. Such control may correspond to a user input or command to effect the operation of the apparatus. The blocks may represent operations in a method and/or sections of instructions/code 1005 in the computer program 1004, e.g. such that the controller might be configured to cause the method 1100 to be performed.

It will be understood that each block and combinations of blocks, can be implemented by various means, such as hardware, firmware, and/or software including one or more computer program instructions. For example, one or more of the procedures described above may be embodied by computer program instructions 1005. In this regard, the computer program instructions which embody the procedures described above may be stored in the memory storage device 903 and performed by the processor 1002.

As will be appreciated, any such computer program instructions may be loaded onto a computer or other programmable apparatus (e.g., hardware) to produce a machine, such that the instructions, when performed on the programmable apparatus, create means for implementing the functions specified in the blocks.

The computer program instructions may also be loaded onto a programmable apparatus to cause a series of operations to be performed on the programmable apparatus to produce a computer-implemented process such that the instructions which are performed on the programmable apparatus provide operations for implementing the functions specified in the blocks.

Figure 12A:
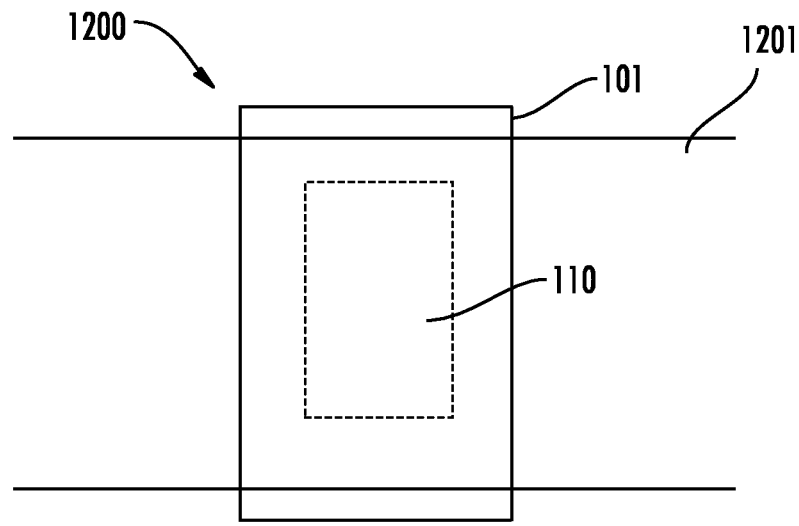
FIGS. 12A and 12B schematically illustrate top and side views of an apparatus on a user according to example embodiments of the present disclosure.
Figure 12B:
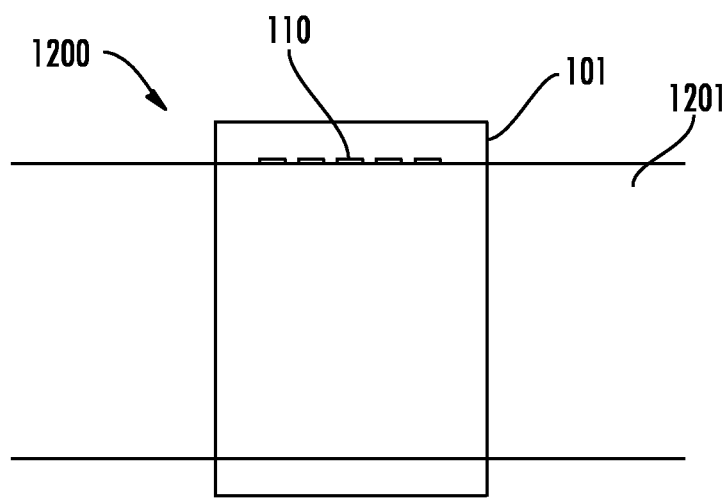

FIGS. 12A and 12B schematically illustrate top and side views of an apparatus on a user according to example embodiments of the present disclosure. FIG. 12A illustrates a top view of the apparatus 1200 on a user's torso/appendage 1201. FIG. 12B illustrates a side view of the apparatus 1200 on the user's torso/appendage 1201. The apparatus 1200 comprises a support structure 101 and an adaptive sensor module 110 (outlined). The adaptive sensor module 110 is proximal to the torso/appendage 1201. As shown in FIGS. 12A and 12B, the apparatus 1200 may at least partially enclose the torso/appendage 1201 of the user.

In alternative embodiments, a section of circuitry may be located outside of the support structure, such as on a second support structure. By doing so, the apparatus comprising one or more adaptive sensor modules could be made lighter and smaller. In some embodiments, a second support structure may house the majority of the hardware to control the apparatus comprising one or more adaptive sensor modules (e.g. a power supply, electronic components, user interface and circuitry for controlling the sensors of the adaptive sensor modules), the apparatus comprising the adaptive sensor modules can be made to be lighter than the second support structure and/or thinner than the second support structure, e.g. having one or more dimensions less than those of the second support structure. Advantageously, such an arrangement may give rise to less strain and pressure on the user's torso or appendage when wearing the apparatus. The relatively low mass apparatus comprising one or more adaptive sensor modules can be kept in place with a relatively small force and thus can be tightly fitted to the user's torso or appendage without undue force/digging into the user's torso or appendage causing discomfort.

The relatively higher mass second support structure could be loosely fitted and allowed to move relative to the torso/appendage, thus not obstructing upper skin blood circulation and giving higher levels of comfort. The loosely fitted second support structure could avoid sweating under the second support structure making it possible for air to flow and excess humidity to escape underneath the second support structure. Advantageously, this gives rise to less conducted heat from the second support structure to the user's torso/appendage, and allows for sensor measurements from body and environment to be more easily separated (e.g. the temperature changes of the main electronics unit and energy storage of the second support structure have less effect on the body temperature measurements of the apparatus comprising one or more adaptive sensor modules). The energy storing unit in the relatively loosely fitted second support structure may be replaceable which provides instant recharging.

The second support structure and apparatus comprising one or more adaptive sensor modules may be electrically coupled together and mechanically de-coupled from one another so as to enable relative movement from one another. The provision of two such structures means that one of the structures can easily be replaced thereby readily providing the ability to customize device functions and style.

The second support structure may be disposed adjacent/side-by-side, at least partially overlay, substantially overlays/overlap, or substantially entirely overlay the apparatus comprising one or more adaptive sensor modules.

Although examples of the apparatus have been described above, and are further described below in terms of comprising various components, it should be understood that the components may be embodied in or otherwise controlled by a corresponding processing element or processor of the apparatus. In this regard, each of the components described above may be one of more of any device, means or circuitry embodied in hardware, software or a combination of hardware and software that is configured to perform the corresponding functions of the respective components. Apparatuses in accordance with certain examples of the present disclosure may be configured for: portable use, wearable use (e.g. on a limb portion such as a: wrist, bicep, ankle, etc.) and wired or wireless communication (e.g. via a cellular network, wide area network (WAN) or short range wireless communication protocol).

The apparatus may have additional functions beside communication and comprise: user input interfaces (e.g. buttons, voice control, touch screen, as well as user input by user manipulation of the overall apparatus, e.g. squeezing the apparatus between thumb and forefinger as discussed above) and user output interfaces (e.g. audio-visual and haptic output devices).

In addition to providing sensor measurements and readings, examples of the apparatuses according to the present disclosure may additionally provide one or more audio/text/video communication functions (e.g. tele-communication, video-communication, and/or text transmission (Short Message Service (SMS)/Multimedia Message Service (MMS)/emailing) functions), interactive/non-interactive viewing functions (e.g. web-browsing, navigation, television (TV)/program viewing functions), music recording/playing functions (e.g. Moving Picture Experts Group Audio Layer 3 (MP3) or other formats and/or (frequency modulation/amplitude modulation) radio broadcast recording/playing), downloading/sending of data functions, image capture function (e.g. using a (e.g. in-built) digital camera), and gaming functions.

In the above description, the wording "connect," "couple," "communication" and their derivatives mean operationally connected/coupled/in communication. It should be appreciated that any number or combination of intervening components can exist (including no intervening components).

Features described in the preceding description may be used in combinations other than the combinations explicitly described. Although functions have been described with reference to certain features, those functions may be performable by other features whether described or not. Although features have been described with reference to certain examples, those features may also be present in other examples whether described or not.

The term "comprise" is used in this document with an inclusive not an exclusive meaning. That is any reference to X comprising Y indicates that X may comprise only one Y or may comprise more than one Y.

While endeavoring in the foregoing specification to draw attention to those features of the invention believed to be of particular importance it should be understood that the applicant claims protection in respect of any patentable feature or combination of features hereinbefore referred to and/or shown in the drawings whether or not particular emphasis has been placed thereon.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An apparatus comprising:
a chassis configured to at least partially enclose the torso or an appendage of a user;
a spring module disposed on the chassis;
a first section of flexible circuitry disposed on the spring module, wherein the flexible circuitry is disposed on a first surface of the spring module, extended through an opening in the spring module, and disposed on a second surface of the spring module, the second surface opposing the first surface; and
a first sensor disposed on the first section of flexible circuitry and configured to monitor the user, the first section of flexible circuitry comprising at least one device being surface-mounted on a flexible board or printed on a flexible board.

2. An apparatus according to claim 1, further comprising a polymer material disposed at least partially over the first sensor.

3. An apparatus according to claim 1, wherein the chassis comprises an inner support layer and an outer support layer and wherein the spring module, the first section of flexible circuitry, and the first sensor are disposed between the inner support layer and the outer support layer.

4. An apparatus according to claim 1, wherein the spring module comprises one or more of a ledge, dome, foam or spiral spring.

5. An apparatus according to claim 2, wherein the polymer material comprises one or more of poly(methyl methacrylate), polyurethane, epoxy, polyester, polycarbonate, polystyrene, polyetherimide, polyamide, cycloolefin polymer, cycloolefin copolymer, acrylonitrile butadiene styrene, allyl diglycol carbonate, or silicone.

6. An apparatus according to claim 1, wherein the chassis comprises a fastener configured to attach the chassis to the torso or the appendage of the user.

7. An apparatus according to claim 6, wherein the fastener comprises one or more of a belt, a snap, a tie, or an adhesive based attachment mechanism.

8. An apparatus according to claim 1, wherein the chassis comprises one or more of: a power supply, or circuitry configured to control the first sensor.

9. An apparatus according to claim 1, wherein the apparatus comprises a second section of flexible circuitry disposed on the chassis.

10. An apparatus according to claim 1, further comprising one or more second sensors disposed along a length of the chassis and configured to monitor the user.

11. An apparatus according to claim 1, wherein the chassis comprises a user actuation section.

12. An apparatus according to claim 1, further comprising at least one sensor configured to detect user actuation of a part of the apparatus.

13. An apparatus according to claim 12, wherein a sensor signal from the at least one sensor configured to detect user actuation of a part of the apparatus is configured to control the apparatus.

14. An apparatus according to claim 1, further comprising one or more sensors disposed along a length of the chassis and configured to monitor an external environment.

* * * * *